United States Patent
Clostermann et al.

(10) Patent No.: US 9,788,921 B2
(45) Date of Patent: Oct. 17, 2017

(54) RETENTION DIE AND DENTAL IMPLANT SYSTEM

(71) Applicant: ZL Microdent-Attachment GmbH & Co. KG, Breckerfeld (DE)

(72) Inventors: Volkhard-Hagen Clostermann, Hagen (DE); André Manke, Olpe (DE)

(73) Assignee: ZL Microdent-Attachment GmbH & Co. KG, Breckerfeld (DE)

( * ) Notice: Subject to any disclaimer, the term of this patent is extended or adjusted under 35 U.S.C. 154(b) by 0 days.

(21) Appl. No.: 15/028,642

(22) PCT Filed: Sep. 30, 2014

(86) PCT No.: PCT/EP2014/070932
§ 371 (c)(1),
(2) Date: Apr. 11, 2016

(87) PCT Pub. No.: WO2015/055423
PCT Pub. Date: Apr. 23, 2015

(65) Prior Publication Data
US 2016/0250003 A1    Sep. 1, 2016

(30) Foreign Application Priority Data

Oct. 15, 2013  (EP) .................................... 13188761

(51) Int. Cl.
*A61C 8/00* (2006.01)
*A61C 13/265* (2006.01)

(52) U.S. Cl.
CPC .......... *A61C 8/0062* (2013.01); *A61C 8/0012* (2013.01); *A61C 8/0048* (2013.01);
(Continued)

(58) Field of Classification Search
CPC ... A61C 8/0062; A61C 8/0012; A61C 8/0048; A61C 8/0054; A61C 8/0069; A61C 8/006; A61C 13/2656
See application file for complete search history.

(56) References Cited

U.S. PATENT DOCUMENTS

| | | | |
|---|---|---|---|
| 6,190,169 B1* | 2/2001 | Bluemli | A61C 13/2656 433/172 |
| 2009/0011384 A1* | 1/2009 | Collins | A61C 8/0012 433/174 |
| 2012/0003606 A1* | 1/2012 | Fischler | A61C 8/0048 433/141 |

FOREIGN PATENT DOCUMENTS

| | | |
|---|---|---|
| CH | 380292 A | 7/1964 |
| DE | 94 19 173 U1 | 2/1995 |
| DE | 10 2011 081 214 A1 | 2/2013 |

OTHER PUBLICATIONS

European Examination Report in EP 13188761.4-1658, dated Apr. 2, 2014, with English translation of relevant parts.
(Continued)

*Primary Examiner* — Heidi M Eide
(74) *Attorney, Agent, or Firm* — Collard & Roe, P.C.

(57) ABSTRACT

The invention relates to an apparatus for releasable attachment of a removable dental prosthesis to a head part of an implant or of an abutment that can be anchored in an implant, comprising a retention matrix (1) having a receptacle that accommodates a circular-ring-shaped retention element (2) that has at least two clamping arms (22), which is disposed so as to be displaceable along a center axis of the retention matrix (1), wherein the at least two clamping arms (22) form a mantle surface that widens conically toward the outside, and that the receptacle for the retainer element (2) has two sections (14, 15) having a different inside diameter, against the transition of which the at least two clamping
(Continued)

Figure 1:
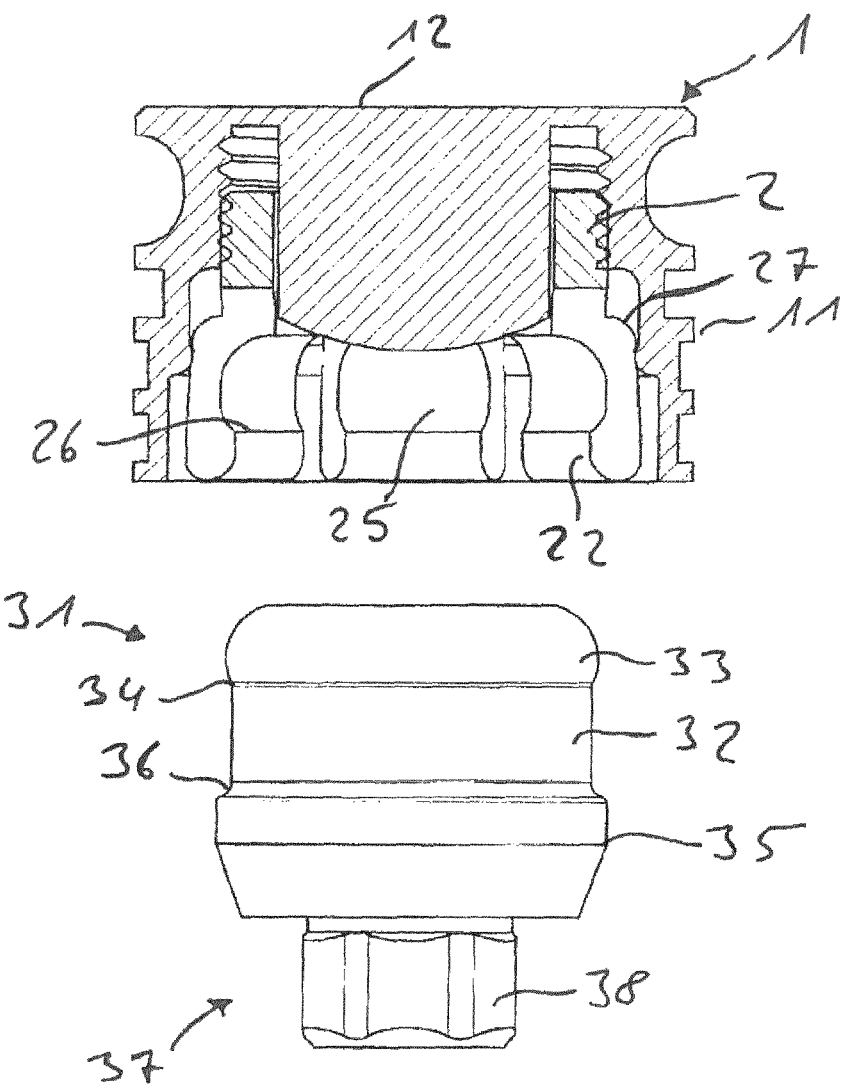

arms (22) lie. The invention furthermore relates to a dental implant system, having such an apparatus.

10 Claims, 2 Drawing Sheets

(52) U.S. Cl.
CPC .......... *A61C 8/0054* (2013.01); *A61C 8/0069* (2013.01); *A61C 8/006* (2013.01); *A61C 13/2656* (2013.01)

(56) References Cited

OTHER PUBLICATIONS

International Search Report of PCT/EP2014/070932, dated Dec. 15, 2014.

\* cited by examiner

RETENTION DIE AND DENTAL IMPLANT SYSTEM

CROSS REFERENCE TO RELATED APPLICATIONS

This application is the National Stage of PCT/EP2014/070932 filed on Sep. 30, 2014, which claims priority under 35 U.S.C. §119 of European Application No. 13188761.4 filed on Oct. 15, 2013, the disclosures of which are incorporated by reference. The international application under PCT article 21(2) was not published in English.

The invention relates to an apparatus for releasable attachment of a removable dental prosthesis to a head part of an implant or of an abutment that can be anchored in an implant, according to the preamble of claim 1. The invention furthermore relates to a dental implant system according to claim 9.

For attachment of removable dental replacements to dental implants, what are called click-head or spherical-head dental implant systems are used, which have a retention matrix having a receptacle in which a retainer element is held. The retention matrix, together with the retainer element, can be releasably fixed in place on an implant and is merely clipped onto the implant, in usual manner. In this regard, the retention matrix is polymerized into a prosthesis base of the dental prosthesis under a defined bite, in order to set the desired prestress of the dental prosthesis against the mucous membrane. The respective holding force of the retention matrix on an implant is established by means of selection of a retainer element that is designed, in terms of its dimensions and its material properties, for the respectively desired holding force or pull-off force. However, even the smallest dimensional inaccuracies of one of these components can already lead to the result that such high pull-off forces are required that it is no longer possible for the user to independently remove the prosthesis from the implant. For this reason, a retention matrix as well as a dental implant system are indicated in DE 10 2011 081 214 A1, in which the said disadvantages are avoided. For this purpose, a clamping ring is provided on the retention matrix, which ring is disposed for a reduction or increase in size of the receptacle. By means of the reduction in size of the receptacle, the retainer element, which lies against the wall of the receptacle, can have a definable prestress applied to it, i.e. it can be compressed on the radial side, as a whole, with elastic deformation of the retainer element.

In CH 380 292 A, an apparatus for releasable attachment of the dental prosthesis to an implant is furthermore described, having a retention matrix with a receptacle that accommodates a retainer element, which element is disposed so as to be displaceable along a center axis of the retention matrix.

The present invention is based on the task of making available an apparatus for releasable attachment of a removable dental prosthesis to a head part of an implant or of an abutment that can be anchored in an implant, in which apparatus a precise adjustment of the pull-off force required for releasing the retention matrix from an implant or an abutment is made possible. According to the invention, the task is accomplished by means of the characteristics of the characterizing part of claim 1.

With the invention, an apparatus for releasable attachment of a removable dental prosthesis to a head part of an implant or of an abutment that can be anchored in an implant is made available, in which apparatus a precise adjustment of the pull-off force required for releasing the retention matrix from an implant or an abutment is made possible. Because of the fact that the at least two clamping arms form a mantle surface that widens conically toward the outside, and that the receptacle for the retainer element has two sections having a different inside diameter, against the transition of which the at least two clamping arms lie, a change in the radial distance of the clamping arms from the center axis is achieved during displacement of the retainer element along the center axis of the retention matrix, thereby making a precise adjustment of the pull-off force possible.

In a further development of the invention, the clamping arms of the retainer element have an indentation on their inside facing away from the retention matrix, forming a negative rounding that forms an undercut. In this way, rotational guidance of the retention matrix on a section of the head part of an implant or of an abutment that can be anchored in an implant, which section corresponds to the indentation, is made possible.

In an embodiment of the invention, a ridge that runs circumferentially, at least in certain sections, is formed onto the transition between the two sections of the receptacle of the retention matrix having a different inside diameter, against which ridge the clamping arms of the retention element lie with their conical mantle surface. In this way, sliding guidance of the clamping arms is achieved.

In a further embodiment of the invention, the clamping arms have a step on the outside, which step lies against the circumferential ridge provided at least in certain sections, in a position of the retainer element. In this way, restriction of a displacement of the retainer element along the center axis of the retention matrix is brought about.

In a further embodiment of the invention, the retainer element has an outside thread that engages into an inside thread disposed in the receptacle, by way of which thread the retainer element can be moved along the center axis of the retention matrix by means of rotation. In this way, the precise adjustment of the pull-off force is supported. In a further development of the invention, a cylinder body is formed in the receptacle of the retention matrix, along the center axis, which body projects axially into the retainer element. In this way, a stop is achieved, in order to guarantee defined positioning of the retention matrix on the head part of the implant.

In a further development of the invention, the cylinder body is configured in cupola shape at its free end. In this way, pivoting of the retention matrix on the head part of the implant in all directions is made possible, thereby achieving precise adaptation to the attachment situation.

The present invention is furthermore based on the task of making available a dental implant system, comprising an abutment that can be anchored in an implant and an apparatus that can be attached to the abutment, of the aforementioned type, which allows precise adjustment of the pull-off force required for releasing the retention matrix from the abutment. According to the invention, this task is accomplished by means of a dental implant system having the characteristics of claim 9.

With the invention, a dental implant system is made available, comprising an abutment that can be anchored in an implant and an apparatus that can be attached to the abutment, of the aforementioned type, in which precise adjustment of the pull-off force required for releasing the retention matrix from the abutment is made possible. The clamping arms accommodate the diameter-widened, circumferentially rounded-off section of the head part of the abutment with their indentation that forms a negative rounding, thereby achieving good rotational guidance. In this regard, the clamping arms lie against the cylindrical section on the end side, thereby furthermore bringing about good support. Further fixation is achieved in that the clamping arms engage behind the undercut disposed in the head part of the abutment, in the installed state of the retention matrix.

In a further development of the invention, the head part of the abutment has a diameter-widening collar on its side of the cylindrical section that lies opposite the rounded-off section, the outside diameter of which collar essentially corresponds to the end-side inside diameter of the retention matrix affixed to the collar. In this way, an axial stop for the retention part, on the head part of the implant, is achieved.

In a further development of the invention, the transition from the cylindrical section of the head part to the diameter-widening collar is formed by a radius, wherein the clamping arms are configured to be rounded off on the end side, corresponding to this radius, against which they lie in an axial end position of the retainer element. In this way, a soft stop is brought about.

Preferably, a diameter-reducing section is formed on the head part of the abutment, which section is provided with an outside polygonal profile, preferably an outside hexagonal profile. In this way, pressure-resistant anchoring of the abutment in an implant is made possible. If the implant is configured in one piece, an implant body can also be formed in instead of the diameter-reducing section that functions as an anchor piece, as it is shown, for example, in DE 2011 081 214 A1. In this case, the abutment is part of the implant body.

Figure 2:
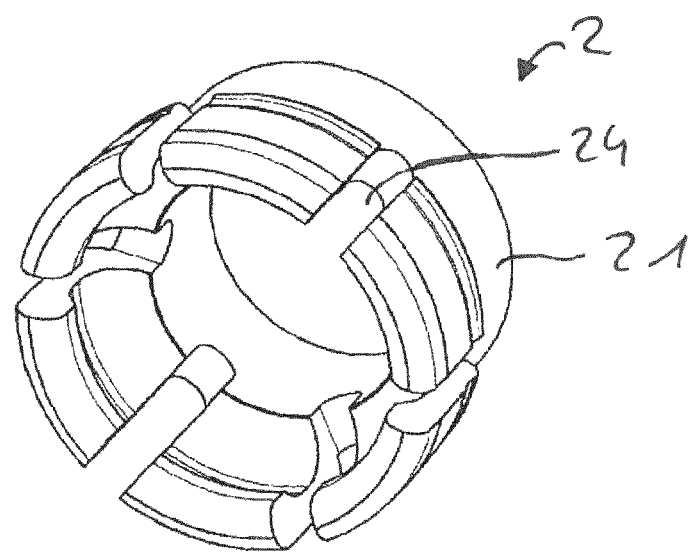
Figure 3:
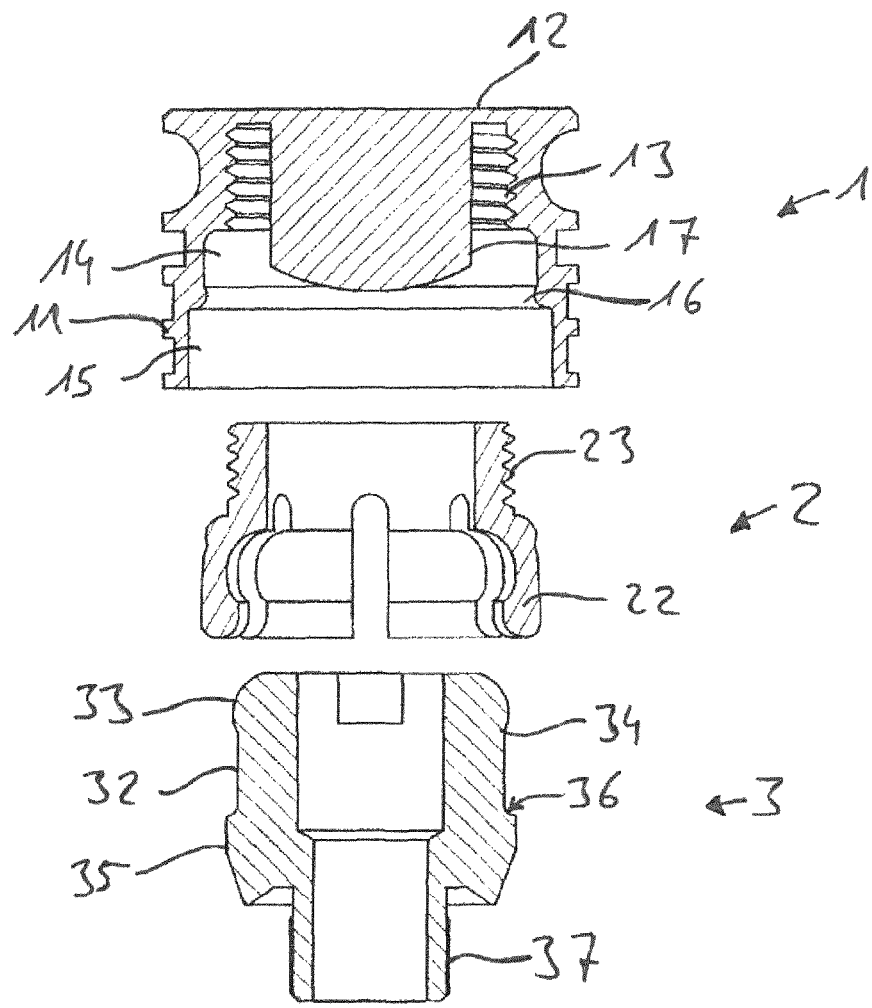
Figure 4:
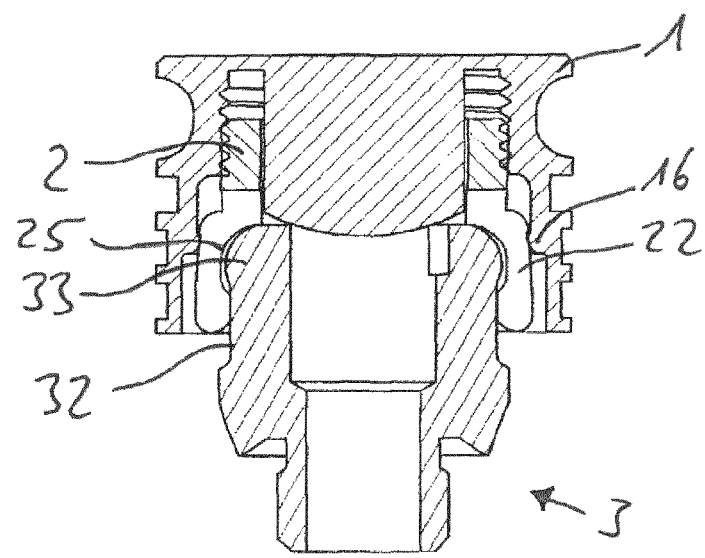

Other further developments and embodiments of the invention are indicated in the remaining dependent claims. An exemplary embodiment of the invention is shown in the drawings and will be described in detail below. The figures show:

FIG. 1 the schematic representation of a retention matrix that accommodates a retainer element, with the head part of an implant brought into position;

FIG. 2 the spatial representation of the retainer element of the arrangement from FIG. 1;

FIG. 3 the schematic representation of a dental implant system in an exploded representation, in longitudinal section, and FIG. 4 the representation of the dental implant system from FIG. 3 in the installed state, in longitudinal section.

The apparatus chosen as an exemplary embodiment consists of a one-part retention matrix 1, which accommodates a retainer element 2, also configured in one part. Together with an abutment 3, which can be anchored in an implant—not shown—this apparatus forms a dental implant system.

The retention matrix 1 is configured as a pot-like titanium part in the exemplary embodiment. Ribs 11 for anchoring in a dental prosthesis—not shown—are formed onto the retention matrix 1, circumferentially on the outside. At its end facing the base 12, an inside thread 13 is introduced into the retention matrix 1 on the inside, followed by a first cylindrical section 14, which makes a transition into a second cylindrical section 15, which is configured with a larger diameter as compared with the first section 14. At the transition between the first cylindrical section 14 and the second cylindrical 15, a rounded-off ridge 16 is formed on circumferentially. In the center, a cylinder body 17 is formed onto the base 12, along the center axis of the retention matrix 1, the free end of which body is configured in cupola shape. The cylinder body 17 projects into the first cylindrical section 14 of the retention matrix 1, wherein the center point of the cupola-shaped end of the cylinder body 17 is disposed approximately at the level of the circumferential ridge 16. The interior configured in this manner forms a receptacle for the retainer element 2.

In the exemplary embodiment, the retainer element 2 is configured as a one-part plastic part. It essentially consists of a circular-ring-shaped base part 21, onto which six clamping arms 22 are formed uniformly over the circumference. The base part 21 is provided with an outside thread 23 on the outside, which thread can be screwed into the inside thread 13 of the retention matrix 1.

The clamping arms 22 are configured to be identical to one another, and are separated from one another by means of slits 24, which project into the base part 21. The circumferentially disposed clamping arms 22 form a mantle surface that widens conically toward the outside, circumferentially on the outside, the smallest diameter of which surface is increased in size as compared with the diameter of the base part 21, wherein the clamping arms 22 are formed onto the base part 21 with radial offset. In this way, a step 27 is formed, which is configured to be rounded off in the exemplary embodiment. On their inside, facing away from the retention matrix 1, the clamping arms 22 are provided with an indentation 25 that forms a negative rounding, by means of which indentation an undercut 26 is formed. On the end side, the clamping arms 22 are configured to be rounded off.

The abutment 3 has a head part 31 on its upper end, having a cylindrical section 32, which makes a transition, on the end side, into a diameter-widened section 33 that is circumferentially rounded off, thereby forming an undercut 34. On its side of the cylindrical section 32 that lies opposite the rounded-off section 33, the head part 31 once again has a diameter-widened collar 35, as compared with the cylindrical section 32, the outside diameter of which collar essentially corresponds to the inside diameter of the second cylindrical section 15 of the retention matrix 1. In this regard, the transition from the cylindrical section 32 of the head part 31 to the diameter-widened collar 35 is formed by a radius 36 that corresponds to the radius of the rounded-off ends of the clamping arms 22. On its end that lies opposite the rounded-off section, the collar 35 is configured to narrow conically.

An anchor piece 37 is formed onto the head part 31 of the implant 3, which piece is circumferentially provided with a hexagonal profile 38. The anchor piece 37 can be anchored, in known manner, in an implant body—not shown—provided with an outside thread. The use of such an abutment proves to be very flexible, because it can be anchored in implants having the most varied embodiments.

The retainer element 2 is screwed into the inside thread 13 of the retention matrix with the outside thread 23 of the base part 21. In this regard, the clamping arms 22 of the retainer element 2 lie against the circumferential ridge 16 of the retention matrix 1. When the retention matrix 1 is set onto the head part 31 of the implant 3, the ends of the clamping arms 22 are elastically moved outward above the ridge 16 of the retention matrix 1, until the rounded-off section 33 of the head part 31 slides into the indentations 25 of the clamping arms 22. In this regard, the cylinder body 17 lies on the level surface of the head part 31 of the abutment 3, thereby achieving a defined axial position of the retention matrix 1 on the abutment 3. The retention matrix is now held on the head part 31 of the abutment 3 in rotatable manner. By means of rotating the retention matrix 1 relative to the retainer element 2, the latter is moved axially in the direction opposite to the head part 31, thereby causing the clamping arms 22 to slide along the ridge 16 and, because of their conical formation, being moved in the direction of the center axis of the retention matrix 1. As a result, the pull-off force is increased. In this regard, the clamping arms 22 slide along the level surface of the cylindrical section 32. In the end position of the retainer element, with maximal pull-off force, the undercut 26 of the clamping arms 22 slides into the undercut 34 of the head part 31.

The invention claimed is:
1. An apparatus for releasable attachment of a removable dental prosthesis comprising
   (a) a retention matrix having a receptacle and a center axis; and
   (b) a circular-ring-shaped retainer element accommodated in the receptacle having at least first and second clamping arms and displaceable along the center axis of the retention matrix;
   wherein the retainer element has an outside thread that engages into an inside thread disposed in the receptacle, wherein rotation of the outside thread moves the retainer element along the center axis of the retention matrix;
   wherein the first and second clamping arms form an outwardly flared conical surface area;
   wherein the receptacle has first and second sections having different first and second inside diameters, respectively, and a transition between the first and second sections;
   wherein the first and second sections are positioned at a distance to the inside thread;
   wherein the first and second clamping arms lie against the transition;
   wherein an at least partially circumferential ridge that runs circumferentially, at least in certain sections, is formed onto the transition between the first and second sections, and
   wherein the conical surface area of the first and second clamping arms lie against the circumferential ridge.
2. The apparatus according to claim 1, wherein the clamping arms of the retainer element have an indentation on an inner side of the clamping arms facing away from the retention matrix, forming a negative rounding that forms an undercut.
3. The apparatus according to claim 1, wherein the clamping arms have an exterior step, wherein the step lies against the at least partially circumferential ridge in one position of the retainer element.
4. The apparatus according to claim 1, wherein a cylinder body is formed in the receptacle of the retention matrix, along the center axis, and projects axially into the retainer element.
5. The apparatus according to claim 4, wherein the cylinder body has a domed-shaped free end.

6. The apparatus according to claim 1, wherein the retainer element is produced from a precious metal or from titanium/a titanium alloy or from a plastic.
7. A dental implant system, comprising
   an abutment having an end side; and
   an apparatus for releasable attachment of a removable dental prosthesis that can be attached to the abutment comprising
   (a) a retention matrix having a receptacle and a center axis; and
   (b) a circular-ring-shaped retainer element accommodated in the receptacle having at least first and second clamping arms and displaceable along the center axis of the retention matrix;
   wherein the retainer element has an outside thread that engages into an inside thread disposed in the receptacle, wherein rotation of the outside thread moves the retainer element along the center axis of the retention matrix;
   wherein the first and second clamping arms form an outwardly flared conical surface area;
   wherein the receptacle has first and second sections having different first and second inside diameters, respectively, and a transition between the first and second sections;
   wherein the first and second sections are positioned at a distance to the inside thread;
   wherein the first and second clamping arms lie against the transition;
   wherein a head part having an outer contour is formed onto the end side of the abutment;
   wherein the head part has a cylindrical section having an end making a transition into a diameter-widened circumferentially rounded section, whereby an undercut is formed, wherein the clamping arms have an indentation corresponding to the outer contour of the head part,
   wherein the clamping arms engage behind the undercut in an installed state of the retention matrix.
8. The dental implant system according to claim 7, wherein the head part of the abutment has a diameter-expanded collar on a side opposite the rounded section, wherein the outside diameter of the diameter-expanded collar substantially corresponds to an end-side inner diameter of the retention matrix mounted on the collar.
9. The dental implant system according to claim 8, wherein the transition from the cylindrical section of the head part to the diameter-expanded collar comprises a radius, wherein the clamping arms have rounded ends corresponding with the radius and lie against the radius in an axial end position of the retainer element.
10. The dental implant system according to claim 7, wherein an anchor piece having a polygonal profile is formed onto the head part of the abutment.

* * * * *